United States Patent [19]

Magnante

[11] 4,146,887
[45] Mar. 27, 1979

[54] RESPIRATOR CARTRIDGE END-OF-SERVICE LIFE INDICATOR

[75] Inventor: Peter C. Magnante, W. Brookfield, Mass.

[73] Assignee: American Optical Corporation, Southbridge, Mass.

[21] Appl. No.: 822,028

[22] Filed: Aug. 5, 1977

[51] Int. Cl.$^2$ .................. G08B 17/10; H01C 13/00
[52] U.S. Cl. .................. 340/632; 338/34; 340/633; 340/636; 128/142.6; 422/96
[58] Field of Search .............. 340/606, 632, 584, 585, 340/595, 622, 603, 633; 338/34; 73/27 R, 204, 295, 23; 23/254 E, 232 E; 128/142.2, 147; 422/96, 97, 98

[56] References Cited

U.S. PATENT DOCUMENTS

| | | | |
|---|---|---|---|
| 2,926,249 | 2/1960 | Rogoff | 73/295 UX |
| 3,059,443 | 10/1962 | Garner | 340/585 X |
| 3,237,181 | 2/1966 | Palmer | 73/27 R X |
| 3,400,582 | 9/1968 | Warner | 73/204 X |
| 3,476,517 | 11/1969 | Smith | 73/27 R X |
| 3,911,413 | 10/1975 | Wallace | 340/632 |
| 3,993,983 | 11/1976 | Meiser | 340/606 X |

*Primary Examiner*—John W. Caldwell, Sr.
*Assistant Examiner*—Daniel Myer
*Attorney, Agent, or Firm*—Jeremiah J. Duggan; H. R. Berkenstock, Jr.; Alan H. Spencer

[57] ABSTRACT

A gas or vapor sensing and alarm device in an air purifying respirator for warning the wearer of hazardous levels of gases or vapors penetrating through the respirator cartridge. An exothermic sensor which can be fitted in the cartridge adaptor or facepiece cavity of the respirator monitors the heat evolved during adsorption of the vapor or gas into the sensor's adsorbent and triggers in alarm when the respirator cartridge has reached the end of its service life.

10 Claims, 4 Drawing Figures

RESPIRATOR CARTRIDGE END-OF-SERVICE LIFE INDICATOR

BACKGROUND OF THE INVENTION

1. Field of the Invention

This invention relates to improvements in respirators and has particular reference to means and method for indicating end-of-service life of respirator cartridges.

2. Discussion of the Prior Art

Respirator cartridges for filtration against vapors or gases are generally filled with adsorbent solids which are able to trap the vapors or gases on their surfaces and cellular interstices. When exposed to adsorbing vapors and gases over a period of time, the available surfaces and interstices of the absorbing solid eventually become filled up and no further adsorption can occur. When this happens to the adsorbent within a respirator cartridge, the cartridge is no longer effective as a filtering device and consequently offers no protection to the respirator wearer.

Because of this danger to the wearer, the use of prior art air purifying respirators for protection against air contaminants having poor warning properties is not recommended. A contaminant has poor warning properties if its odor, taste, or irritation threshold level is greater than the permissable exposure limits, or if there is insufficient toxicological data to determine an exposure limit. Exposure limits for most gases are published regularly by the "American Conference of Governmental Industrial Hygienists".

In many industries, prior art air purifying respirators are used for substances having poor warning properties by implementing special work practices involving determination of the ambient level of the air contaminant and using a respirator cartridge for only a period of time when the protection level that it offers is sufficient to protect the wearer from the hazard at its ambient concentration. Administrative control of chemical vapor respirator cartridge service life is, however, tedious, costly and complex with less than optimum reliability. The U.S. National Institute for Occupational Safety and Health (NIOSH) does not recommend administrative control of respirator cartridge service life and has suggested that when substances with poor warning properties are encountered in the workplace at concentration levels above the permissible exposure limits, other forms of respirators such as air supplied devices be used or that air purifying respirators be equipped with systems which can be relied upon to indicate when they are no longer filtering effectively.

In attempts to accomplish the latter, the prior art includes respirator canisters having windows for detecting change of color of the canister adsorbent or impregnated indicator strips e.g. as in U.S. Pat. No. 1,537,519. Another system for detecting exhaustion of a respirator for protection against carbon monoxide includes a reagent which, on contact with carbon monoxide, will generate a vapor causing irritation of the eyes, nose and/or throat of the wearer as a warning of respirator exhaustion. U.S. Pat. No. 1,414,194 is exemplary. Also well known is an arrangement for detecting carbon monoxide utilizing a material called Hopcalite which interacts with carbon monoxide to produce carbon dioxide and heat. The carbon dioxide is then utilized to produce a color change in an adsorbent which indicates the original presence of carbon monoxide.

Chemically treated filters can provide color indication of moisture content of air discharged from the filter as in U.S. Pat. No. 2,528,539, for example, and electrolytic oxygen sensors in rebreathing apparatuses have been used, e.g. as in U.S. Pat. No. 3,695,261 to operate exhaust valves, warning lights or meters.

Carbon dioxide adsorbing apparatuses applied to patients undergoing anesthesia are also well known in the art. These apparatuses may embody indicator agents which change color in the course of absorption and depletion of the absorbtive capacity of the devices.

While the aforesaid various forms of prior art respirator cartridge residual life or exhaustion indication and/or breathing control systems may in some cases serve their respective purposes very well, those intended for protection against toxic vapors and gases having poor warning properties generally fall short of meeting present day requirements in a manner of readily acceptable efficiency.

It having been discovered according to this invention that the exothermic process between a respirator adsorbent and the adsorbate (vapors or gas adsorbed) may be utilized in end-of-service life detection rather than the approaches of the prior art, a principal object of the invention is to provide for reliable vapor-gas respirator cartridge end-of-service life indication utilizing the aforesaid exothermic process and to provide for reliable visual or audio warning of cartridge failure, i.e. failure to provide respirator protection at or above a hazard concentration level that is considered safe to inhale.

More particularly, it is another object of the invention to provide for positive indication of cartridge exhaustion independently of a user's physical senses of taste, smell or sensation of irritation and further independently of environmental organic vapor or gas concentrations and variations thereof in the course of respirator use.

Other objects and advantages of the invention will become apparent from the following description.

SUMMARY OF THE INVENTION

The aforesaid objects and their corrolaries are accomplished according to the invention by the provision of a gas or vapor exothermic sensor which can be fitted into the cartridge adaptor of a respirator to monitor the heat involved during adsorption of the vapor or gas into the sensor's absorbent. The sensor is placed in an electrical circuit with a miniature power supply and alarm device and, acting as a thermocouple for example, activates the electrical circuits and alarm when the respirator cartridge has exceeded its service life.

Details of the invention will become readily apparent from the following description when taken in conjunction with the accompanying drawings.

IN THE DRAWINGS

DESCRIPTION OF THE PREFERRED EMBODIMENTS

Figure 1:
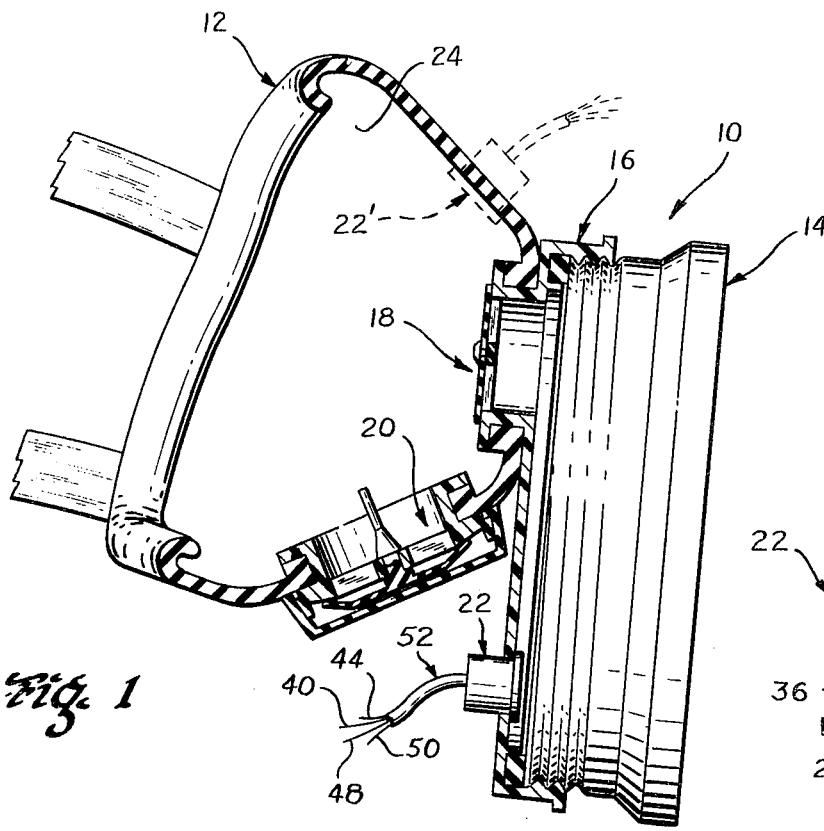
FIG. 1 is a partially cross-sectioned illustration of an air purifying respirator embodying cartridge end-of-service life sensing means according to the invention.

When a gas or vapor is adsorbed by a solid, heat is always released in the process (exothermoic). The amount is quite large, typically 10°-15° C. for activated charcoal absorbing ethyl chloride, for example. The amount of heat generated depends on the amount of adsorbent, the amount of adsorbate (the vapor or gas absorbed), and a coefficient characterizing both adsorbent and adsorbate, called the differential heat of adsorption. It is well known that tabulations of these coefficients exist in the literature, e.g. The Surface Chemistry of Solids, S. J. Gregg, Reinhold Publishing Corp., New York, 1951.

The particular exothermic sensor relating to the present invention is a temperature sensitive device having an "active element", such as a thermocouple surrounded by a vapor absorbent material and which is capable of activating an electrical circuit and alarm. The temperature sensed (and the consequent electrical signal which drives the circuit) depends on the heat evolved during the adsorption of the vapor or gas into the adsorbent, e.g. activated charcoal, within which the particular temperature sensitive device is imbedded. The heat of absorption coefficients for most organic vapors do not differ appreciably (i.e. less than a factor of 2-3) so that the present system is applicable to use in atmospheres of most, if not all, toxic vapors and gases.

The actual temperature achieved depends, of course, on inevitable heat loss processes from the adsorbent. These losses will be caused primarily by conductive phenomenon such as heat flow into material in contact with the adsorbent and convective phenomenon such as exchange with the ambient air. In order to maximize the temperature during the adsorption, and thereby the signal, the present invention contemplates insulation of the exothermic sensor against at least a substantial part of the aforesaid heat losses. This, as it will become more readily apparent hereinafter, may be accomplished with a porous or otherwise vented heat shield which surrounds the exothermic sensor but allows a slow transport of gases and vapors thereto.

In order to stabilize the exothermic sensor from ambient temperature changes, it is contemplated that a "reference element" be incorporated to cancel out signals caused by ambient temperature fluctuations which may drive the "active element" in the same way that temperature increases due to adsorption may drive the "active element". This cancellation of ambient temperature fluctuations is presently accomplished by making the "reference element" identical to the "active element" except that it lacks the adsorbent material. The "active element" and "reference element" are electrically connected in series before coupling to the electronic circuit.

A desirable additional element of the exothermic sensor is a coil of high resistance metal wire which may be used to heat the adsorbent material during periodic checks of the system in order to drive off contaminating vapors or gases accumulated from prior uses.

Referring more particularly to the drawings, there is illustrated in FIG. 1 an exemplary form of respirator 10 having facepiece 12, air purifying cartridge 14, cartridge adaptor 16 into which the cartridge is manually removably threaded, inhalation valve 18 and exhalation valve 20. All such components of respirator 10 are conventional and typical of the type of respirator illustrated. This invention, however, is not in any way limited or restricted to the style or type of respirator illustrated in FIG. 1. Other forms such as the full-face type respirator or gas mask with either cartridge or cannister may be equipped according to the present invention for cartridge end-of-service life indication.

The combined "active element" - "reference element" exothermic sensor 22 (FIG. 2) may be placed in the cavity of cartridge adaptor 16 through which inhaled air passes from cartridge 14 to inhalation valve 18. This is shown with full line illustration of sensor 22 in FIG. 1. Alternatively, the sensor can serve the dual purpose of detecting end-of-service life of cartridge 14 and indicating dangerous leakage around the respirator facepiece or elsewhere when the respirator is in use. This may be accomplished by placing sensor 22 in the cavity 24 of facepiece 12 as illustrated with broken lines 22'. Sensor 22' is identical to sensor 22.

Referring more particularly to details of exothermic sensor 22, a desirable embodiment thereof may comprise a supporting shell 26, e.g. of molded plastic, which is at least partially perforated at end 28. In the final assembly of sensor 22 in respirator 10 (FIG. 1) its end 28 is disposed inwardly of the cartridge adaptor cavity or facepiece cavity as the case may be. Internally of shell 22 there is provided a pair of preferably identically shaped and sized compartments 30 and 32 into each of which an identical temperature-electronic transducer is positioned. These transducers 34 and 36 are preferably positioned adjacent to the perforations in end 28 of shell 26. They may comprise any one of various well known temperature-electronic devices such as, for example, a thermocouple, thermistor, bolometer, heat sensitive diode or in each case of each transducer 34 and 36 more than one of the aforesaid devices wired together in series or parallel to optimize an electrical signal produced by them as a result of their additive temperature increases. It is contemplated that the device of each transducer 34 and 36, in whatever form selected, will have a small mass and large electric response to temperature change coefficient.

Transducer 34 which will be referred to hereinafter as the "active element" is surrounded with adsorbent material 38 which may, for example, be in granular form. A desirable adsorbent, e.g. one exhibiting a large heat release (10° - 15° C.) in the exothermic process is activated charcoal when in the presence of ethyl chloride. Granular activated charcoal is a typical organic vapor adsorbent and commonly used in organic vapor respirator cartridges such as cartridge 10.

Other useful adsorbents are silica gel, alumina, ferric oxide and other available commercial substances such as porous polymer gas chromotography packings with a volume no larger than approximately 1 $cm^3$ and no smaller than approximately 0.1 $mm^3$, in any shape whatsoever.

Transducer 36 which will be referred to hereinafter as the "reference element" is also placed adjacent to the perforations in end 28 of shell 22 but within compartment 32 which is free of adsorbent material thereby leaving element 36 directly exposed to ambient air in the vicinity of active element 34 and free to sense the temperature of this ambient air at all times. These active and reference elements are electrically interconnected by leads 40, 42 and 44.

A coil of high resistance metal wire 46 is wrapped around the adsorbent 38 for selectively heating adsorbent 38 sufficiently e.g. as high as 300° C., to drive off vapors or gases accumulated therein from prior use or other exposure. Electrical leads 48 and 50 may be used to supply an operating electrical current to the coil, e.g. in the manner illustrated in FIG. 4. The coil 46 may encircle both of compartments 30 and 32, if desired. While shell 26 is illustrated in fragmentary cross section for convenience of diagrammatically illustrating the various electrical connections made with electrical leads 40, 44, 48 and 50, its end copposite to end 28 would preferably be closed and sealed about leads 40, 44, 48 and 50 in the manner illustrated in FIG. 1. For example, these leads may be juxtapositioned in a cable and terminally connected into a pocket-size or smaller electrical power supply and control circuit such as one of the types schematically illustrated in FIGS. 3 and 4. It should also be understood that shell 26 may, in place of the perforations at end 28, be provided with an end piece of open cell, i.e. porous ceramic or plastic material for allowing the passage of air and gases thereinto and around transducers 34 and 36. In all cases, the porousities or perforations are so disposed inwardly of the respirator that external atmospheres will not contaminate the system of transducers 34 - 36 and adsorbent 38.

Figure 3:
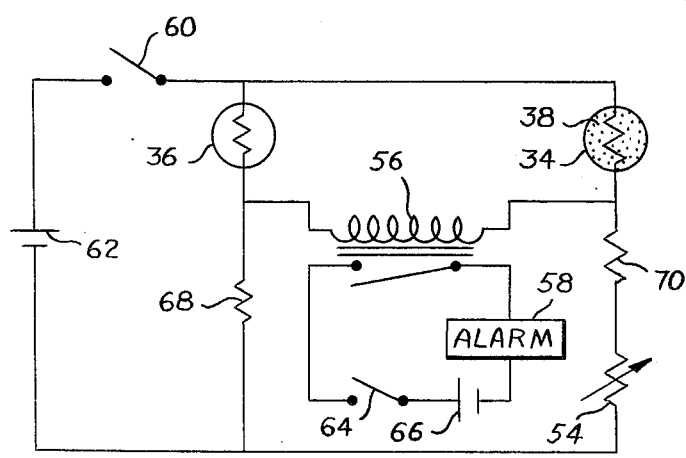
FIG. 3 is an electrical schematic of a basic indicator system contemplated by the invention.

Referring more particularly to FIG. 3, it will be recognized that transistors 34 and 36, i.e. active element 34 and reference element 36 are schematically illustrated in the circuitry for ease and clarity of illustration. They are, of course, normally physically remote from remaining components of the illustrated circuit, i.e. located in sensor 22, and only electrically wired to the other components of the FIG. 3 circuit. These latter components would ordinarily be separately contained in a small box, the box in turn placed in a shirt pocket for example and the sensor 22 in the respirator.

Figure 4:
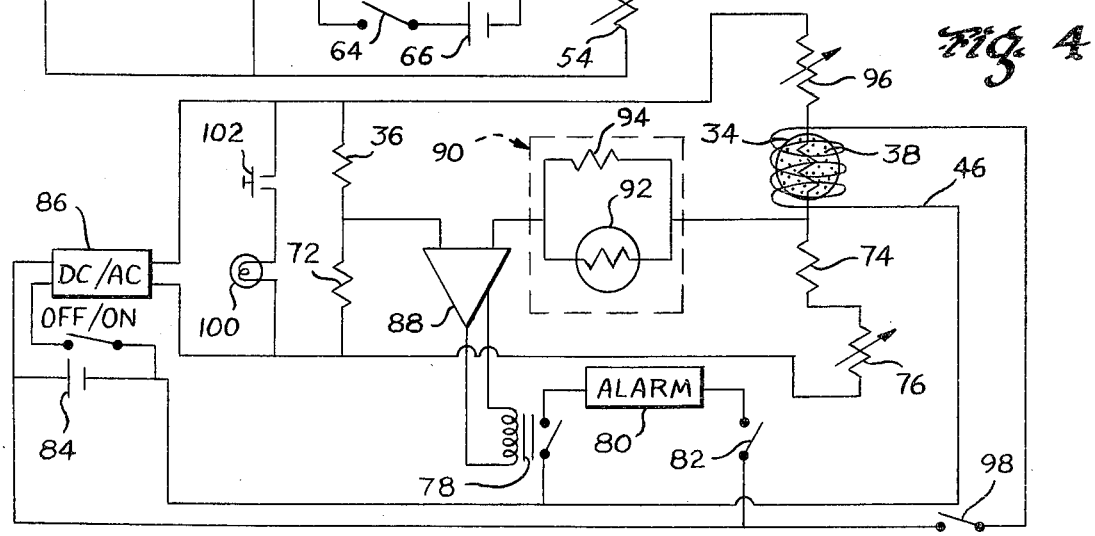
FIG. 4 is an electrical schematic of an alternative form of indicator system.

The circuit of FIG. 3 does not include ancilliary devices such as heating coil 46, the DC/AC electrical converter, AC amplification means, automatic gain control and switching alarm level means such as are included in the more sophisticated system of FIG. 4.

The basic circuit of FIG. 3 is, as can be seen, a Wheatstone Bridge with two arms containing the active and reference elements 34 and 36 respectively. Trim potentiometer 54 is used to balance the bridge in a conventional manner so that no current flows through relay 56 when the transducers of active element 34 and reference element 36 are at the same temperature. When a difference of temperature exists between active element 34 and reference element 36 due to adsorption or desorption of vapors in the adsorbent 38, the bridge becomes out of electrical balance and relay 56 closes to activate alarm 58. Alarm 58 may, of course, comprise any of various means such as an electric light, light emitting diode, small noise emitting horn, buzzer and/or the like. Switch 60 may be provided to open and close the circuit of FIG. 3. Battery 62 (e.g. a nine volt cell) provides the source of direct current.

In the alarm circuit, switch 64 which is normally closed may be selectively opened to deenergize the alarm after it is tripped by relay 56 or whenever else desired. Battery 66 (e.g. a nine volt dry cell) powers the alarm circuit.

Figure 2:
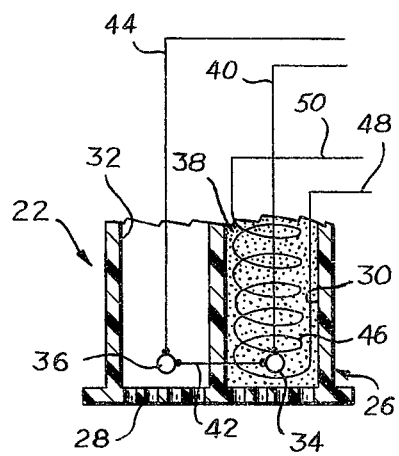
FIG. 2 is an enlarged fragmentary cross-sectional view of the sensing means with electrical components thereof illustrated schematically.

Resistors 68 and 70, together with trim potentiometer 54, are provided to electrically balance the bridge. Active and reference elements 34 and 36 being contained in the construction of sensor 22 (FIGS. 1 and 2) and physically remote from remaining components of the FIG. 3 circuit are connected thereto with cord or cable 52 (FIG. 1) which contains leads 40 and 44 (FIG. 2).

The more elaborate circuitry of FIG. 4 is also in the basic form of a Wheatstone Bridge into which the active element 34 and reference element 36 of sensor 22 are electrically interconnected with the usual balancing resistance elements 72, 74 and trim potentiometer 76. Latching relay 78 activates alarm 80 when the alarm circuit switch 82 is closed and when an electrical imbalance of the bridge circuit occurs due to differential heating of the active and reference elements 34 and 36. The alarm circuit is powered by battery 84 and the bridge in this case is preferably, in turn, energized through a DC/AC converter 86. AC bridges are generally more sensitive and stable than DC bridges.

In the bridge circuit, a high gain AC amplifier 88 may be included for increasing sensitivity to temperature imbalances between elements 34 and 36, e.g. to the extent of imbalances as small as 0.001° C. Such amplifiers are commonly available and well known to those having ordinary skill in the art.

The FIG. 4 bridge circuit may also, if desired, include ambient temperature compensating means 19 for automatically controlling gain and switching (alarm) level with large ambient temperature changes. This means may include thermally variable and fixed resistances 92 and 94 respectively placed in electrically parallel relationship. Variable resistor 96 may be used to adjust the switching (alarm) level.

Heating coil 46 is selectively energized by switch 98, the coil 46 being in series circuit with battery 84.

Lamp 100 and press-to-test button 102 are connected in series across the FIG. 4 AC circuit for use in testing for the existence of electrical operating power before use of the system, i.e. detecting a spent battery.

In a reduction to practice of the invention by laboratory experiment, its operability and applicability to respirator cartridge end-of-service life indication was established. The experiment included the following:

Onto a 10 mil wire size thermocouple was adhered several grains of activated charcoal of the type conventionally used in organic vapor respirator cartridges. The thermocouple was attached to the input of a temperature recorder and the laboratory temperature was noted to be 25° C.

When vapors from a bottle of trichloroethylene were allowed to flow past the tip of the thermocouple having the attached activated charcoal pieces, the temperature rose to 30° C. and when the vapors were removed, the temperature decreased.

Relocating the same thermocouple (i.e. with charcoal) in the trichloroethylene vapor resulted in repeated temperature surges. Prolonged exposure in the vapor, however, resulted in vapor saturation of the charcoal adsorbent and reduced temperature measurements. This indicated the desirability of periodically restoring the charcoal adsorbent, e.g. by heating the adsorbent solid sufficiently to drive off the residual vapors. A temperature near but under 300° C. will produce desirable results.

It was further demonstrated in the laboratory experiment that by removal of the activated carbon pieces from the thermocouple and repeating the procedure of exposure to trichloroethylene vapors with and without removal of the cement, no change of temperature effect was observed. Accordingly, the temperature increase due to the exothermic process between activated charcoal and trichloroethylene was easily measured and the system installed in a respirator will efficiently and reliably function as means for detecting the presence of harmful organic vapors penetrating through spent respirator cartridges and/or leakage around a respirator facepiece.

Those skilled in the art will readily appreciate that various modifications and adaptations of the invention other than those used here for illustration may be made to suit particular requirements. Accordingly, the foregoing illustrations of preferred embodiments of the invention are not to be interpreted as restrictive beyond the extent necessitated by the following claims.

I claim:

1. A toxic gas and vapor sensor comprising:
   a temperature-electronic transducer embedded in a toxic gas and vapor adsorbent, the transducer being electrically responsive to the exothermicity of said adsorbent and its adsorbate when said adsorbent is exposed to toxic gases and vapors;
   means for at least partially insulating said transducer and adsorbent against heat loss; and
   a second temperature-electronic transducer in spaced juxtaposition with said embedded transducer, said second transducer being free of said adsorbent and spaced away therefrom.

2. A sensor according to claim 1 further including electrical heating means adjacent to said imbedded transducer for use in driving off prior use adsorbates before reuse of said sensor.

3. An end-of-service life indicator for respirator cartridges comprising:
   a toxic gas and vapor sensor having juxtapositioned "active" and "reference" elements;
   said active element comprising a first temperature-electronic transducer imbedded in a toxic gas and vapor adsorbent, the transducer being electrically responsive to variations in its ambient temperature and the exothermicity of said adsorbent and its adsorbate when exposed to toxic gases and vapors;
   said reference element comprising a second temperature-electronic transducer having substantially identical electrical response characteristics to those of said first transducer, said second transducer being spaced away from said adsorbent and electrically responsive only to its ambient temperature, the proximity of said active and reference elements being such that their respective ambient temperatures are substantially identical at all times;
   electrically energized circuit means into which said active and reference elements of said sensor are electrically balanced in the absence of toxic gases and vapors; and
   alarm means for alerting attention to an exothermicity in said active element resulting from exposure of the sensor to toxic vapors and gases and causing electrical imbalance of said circuit, the presence of which may indicate an end of the service life of a respirator cartridge next to which said sensor may be placed for monitoring the filtering efficiency of said cartridge.

4. An end-of-service life indicator according to claim 3 including electrical heating means adjacent to said imbedded first transducer for driving off residual prior use adsorbates before reuse of said sensor.

5. An end-of-service life indicator according to claim 4 wherein said heating means includes a coil of high electrical resistance wire.

6. An end-of-service life indicator according to claim 3 wherein said electrically energized circuit comprises:
   a Wheatstone Bridge having two arms, said active element being electrically series connected in one of said arms and said reference element being electrically series connected in the remaining arm;
   electrical relay means connected across said arms, said relay means being activable by electrical imbalance of said bridge; and
   an electrical alarm means in turn activable by activation of said relay.

7. An end-of-service life indicator according to claim 6 wherein said bridge is energized by direct current.

8. An end-of-service life indicator according to claim 6 wherein said bridge is energized by alternating current.

9. An end-of-service life indicator according to claim 8 including alternating current amplifying means in said electrical connection across said bridge for amplifying electrical current produced by imbalance of said bridge and directed to said relay.

10. An end-of-service life indicator according to claim 9 further including electrical means for selectively adjusting the level of sensitivity of said end-of-service life indicator to activation of said relay.

* * * * *